(12) United States Patent
Berberich

(10) Patent No.: US 8,821,411 B2
(45) Date of Patent: Sep. 2, 2014

(54) MEDICAL TOOL

(71) Applicant: Sascha Berberich, Tuttlingen (DE)

(72) Inventor: Sascha Berberich, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 13/959,259

(22) Filed: Aug. 5, 2013

(65) Prior Publication Data

US 2014/0039239 A1 Feb. 6, 2014

(30) Foreign Application Priority Data

Aug. 3, 2012 (DE) .................... 10 2012 107 147

(51) Int. Cl.
*A61B 5/00* (2006.01)

(52) U.S. Cl.
USPC ........................................ 600/564

(58) Field of Classification Search
USPC ................................. 600/564–567
See application file for complete search history.

(56) References Cited

U.S. PATENT DOCUMENTS

| 2,436,538 | A | | 2/1948 | Wing, Sr. |
| 4,810,148 | A | | 3/1989 | Aisa et al. |
| 5,713,368 | A | * | 2/1998 | Leigh ............................ 600/566 |
| 7,946,988 | B2 | * | 5/2011 | Cai et al. ....................... 600/442 |
| 8,444,572 | B2 | * | 5/2013 | Tanaka .......................... 600/564 |
| 8,540,674 | B2 | * | 9/2013 | Kassab et al. ............. 604/164.01 |
| 8,602,974 | B2 | * | 12/2013 | Goldwasser et al. ......... 600/115 |

FOREIGN PATENT DOCUMENTS

| CN | 201164500 Y | 12/2008 |
| DE | 2738693 A1 | 3/1979 |
| DE | 69317699 T2 | 11/1998 |
| DE | 60122936 T2 | 6/2007 |
| DE | 102006034756 A1 | 1/2008 |
| DE | 102009010561 A1 | 8/2010 |
| EP | 0576306 A1 | 12/1993 |
| EP | 0882510 A1 | 12/1998 |
| EP | 1373676 B1 | 1/2004 |
| EP | 1797824 A1 | 6/2007 |
| WO | 02081859 A1 | 10/2002 |
| WO | 2008011308 A2 | 1/2008 |

* cited by examiner

*Primary Examiner* — Max Hindenburg
(74) *Attorney, Agent, or Firm* — St. Onge Steward Johnston & Reens LLC

(57) ABSTRACT

A medical tool for removing tissue includes a removing device for the mechanical removal of tissue, and a magnet for the magnetic attraction and collection of magnetic or magnetizable particles.

15 Claims, 3 Drawing Sheets

MEDICAL TOOL

FIELD OF THE INVENTION

The present invention relates to a medical tool for removing tissue, to a medical instrument with such a tool, and to a method for removing tissue. The present invention relates in particular to the removal of bone tissue or other hard tissue which can cause abrasion of the tool.

BACKGROUND OF THE INVENTION

DE 10 2006 034 756 A1 and DE 10 2009 010 561 A1 each describe a medical instrument for cutting tissue. A tubular inner shank rotates inside a tubular outer shank. Outer shank and inner shank each have windows with blades. Tissue that is cut off by interaction of the blades on the outer shank and on the inner shank is sucked out through the inner shank.

Especially when removing bone tissue or other hard and/or tough tissue, medical personnel often apply considerable forces and torques to the proximal end of the medical instrument in order to press the distal end, for example, with the greatest possible force against a tissue surface that is to be worked. These forces and torques can deform the medical instrument (in general elastically) and in particular bend a shank of the medical instrument.

The described deformation of the medical instrument and/or other causes can have the effect that the inner shank is displaced or tilted with respect to its intended position relative to the outer shank. The inner shank and the outer shank can thus touch each other in a way that is not intended. Contact between the inner shank and the outer shank, in particular between the blades on the inner shank and outer shank, can increase the wear of both and can cause abrasion in the form of fine particles or even the breaking-off of larger particles.

Particles generated in the described manner, or in some other way, are foreign bodies that should not remain at the operating site. The particles are sucked or scraped off, for example, with or without the use of a flushing liquid. With a suitable choice of the materials of the medical instrument, it is true that particles nonetheless remaining in the operating site do not have any toxic effect. However, the particles can have a mechanically disadvantageous effect and can, for example, cause artefacts in subsequent X-rays. Abrasion of medical instruments and the avoidance and/or removal of the abraded material are therefore challenges that still have to be tackled.

SUMMARY OF THE INVENTION

It is an object of the present invention to make available an improved medical tool, an improved medical instrument and an improved method for removing tissue.

This object is achieved by the subjects of the independent claims.

Developments are set forth in the dependent claims.

It is traditionally sought to minimize wear and abrasion through suitable materials and suitable shaping. It is also sought to ensure that an unavoidable minimum amount of abraded material can be removed by suction during the removal of tissue or in a subsequent method step. By contrast, embodiments of the present invention are based on the concept whereby particles that are generated by abrasion or in another way are collected by means of a magnet arranged on the medical tool itself.

Whereas conventional medical instruments are generally made mainly or exclusively of non-magnetic and non-magnetizable materials (in particular stainless steels), the present invention entails the use of magnetic or magnetizable materials at least in the area of surfaces that may be affected by abrasion or erosion.

Following notification of the present invention, patent specialists from the patent division of the Applicant carried out a search using abstracted search terms. The identified documents are briefly discussed below although, for a number of reasons, they would not have been taken into account by specialists who had been given the task of achieving the above-mentioned object.

EP 0 576 306 B1, also published as DE 693 17 699 T2, describes a magnetic detector which is provided for arrangement in a flow of fluid. An alarm is intended to be triggered after a predetermined quantity of metal particles has been taken up.

U.S. Pat. No. 4,810,148 and EP 0 882 510 A1 describe screws with magnets, around which a circulating lubricant is intended to be flushed. Abraded metallic material contained in the circulating lubricant is intended to remain adhering to the magnets.

WO 02/081859 A1, also published as EP 1 373 676 A1 and DE 601 22 936 T2, describes a device for recovering abraded metallic material from a well bore, which device has a plurality of magnets.

None of the identified documents has any connection with medical technology or suggests any possibility of application to solving medical problems. Moreover, the first three documents mentioned, i.e. EP 0 576 306 B1, U.S. Pat. No. 4,810, 148 and EP 0 882 510 A1, have no connection of any kind to the working of a surface. Moreover, in complete contrast to the present invention, they are intended to be flushed by a medium that contains abraded metallic material. Although the last-mentioned document, i.e. WO 02/081859 A1, has a connection with mechanical working, albeit also in a non-medical context, a separate device is provided for the collection of abraded metallic material. A combination with a machining tool itself is neither described nor even simply suggested or obvious to specialists proceeding from WO 02/081859 A1.

In the present invention, magnetic or magnetizable means any material that has not only diamagnetic properties. Magnetic or magnetisable within the meaning of this present patent application are in particular paramagnetic, ferromagnetic, anti-ferromagnetic and ferrimagnetic materials. In other words, magnetic or magnetizable refers here to all materials on which, in an inhomogeneous magnetic field, a force acts in a direction to a location with a higher magnetic field strength.

Bodies having a magnetic or magnetizable material of this kind are, for example, attracted by a pole of a dipole magnet. By contrast, in an inhomogeneous magnetic field, diamagnetic materials experience a force in the direction of a location with a lower magnetic field strength. A body made of a diamagnetic material is therefore repelled from a pole of a dipole magnet. A material that has only diamagnetic properties is not here designated as magnetic or magnetizable.

A medical tool for removing tissue comprises a removing device for the mechanical removal of tissue, and a magnet for the magnetic attraction and collection of magnetic or magnetizable particles.

The medical tool is in particular a milling device or a shaver. The medical tool is provided and designed for use on or with a medical instrument, to which it can be connected so as to be releasable without destruction. Alternatively, the medical tool can be a permanent component of a medical instrument and is not releasable from the medical instrument without destruction. The medical tool is provided and designed in particular for microinvasive procedures.

The removing device is arranged in particular at the distal end or near the distal end of the medical tool and is designed in particular for removing bone or cartilage tissue or other solid, hard and/or tough tissue. The removing device can have one or more geometrically defined blades, for example in the manner of a milling cutter or a drill. Alternatively, the removing device can have geometrically undefined blades. The magnet is provided and designed in particular for the magnetic attraction and collection of particles that arise as a result of abrasion, erosion or other kinds of wear of the removing device.

Magnetic attraction and collection of magnetic or magnetizable particles can in many cases partially or completely replace the shaving of surfaces, which is potentially traumatic or causes additional trauma. Independently of its own properties and of the magnetic properties of the particles, the magnet can then easily attract and collect the particles even if they are pressed completely or partially into a soft surface for example. The magnet permits a selective interaction with magnetic or magnetizable particles, without in so doing influencing surrounding tissue. The described medical tool is thus suitable for reducing trauma.

The integration of the removing device and of the magnet in a single medical tool can permit collection and withdrawal of magnetic or magnetizable particles simultaneously with the removal of tissue, or in a separate method step directly thereafter, using the same medical tool. The use of the medical tool is therefore advantageous in terms of time expenditure and therefore also from the medical and economic points of view.

In a medical tool as described here, the magnet is arranged in particular on a component of the tool that is substantially stationary during removal of tissue.

The magnet is arranged in particular on a component of the tool which, during the removal or tissue, is moved only linearly, in particular only slowly linearly, and does not rotate. The component that does not rotate or that is substantially stationary during the removal of tissue comprises in particular an outer shank or a distal end of an outer shank of the medical tool.

In a medical tool as described here, the removing device comprises in particular a first component and a second component, wherein the second component is movable relative to the first component in order to remove tissue, wherein the magnet is arranged on the first component, and wherein a blade is arranged on the second component.

The second component is in particular rotatable relative to the first component and to a tissue that is to be removed. In other words, the medical tool is designed to remove tissue by rotation of the second component relative to the first component. The second component also rotates relative to a maneuvering device at the proximal end of a medical instrument, of which the medical tool can be a permanent or temporary constituent part.

The first component is or comprises in particular an outer shank or a distal end of an outer shank of the medical tool. The second component is or comprises in particular an inner shank, which is rotatable relative to the outer shank and on which is arranged a blade that is rotatable with the inner shank. A blade can likewise be arranged on the outer shank and is substantially stationary, or at least does not rotate, during the removal of the tissue.

The arrangement of the magnet on a component that is substantially stationary during the removal of tissue can permit a good relationship between a cross section of a lumen in a rotating component and an overall cross section of the medical tool. Moreover, the arrangement of the magnet on a component that is substantially stationary during the removal of tissue can permit more installation space for the magnet and, if appropriate, for a reservoir for receiving particles attracted and collected by the magnet. In this way, the efficiency in terms of the collection and withdrawal of magnetic or magnetizable particles can in particular be greater than in an arrangement of the magnet on a component that rotates or is otherwise moved during the removal of tissue.

In a medical tool as described here, the magnet is in particular arranged and designed to collect particles during removal of tissue.

For this purpose, the magnet is in particular arranged alongside the removing device in such a way that a surface (in particular a plane surface) worked by means of the removing device at the same time lies opposite the magnet and in the magnetic near field thereof.

In a medical tool as described here, the magnet is in particular arranged and designed to collect particles in a separate method step after removal of tissue.

For this purpose, the magnet is in particular arranged in such a way that tissue can first of all be removed from a surface by means of the removing device, and, after a rotation of the medical tool about its longitudinal axis, magnetic or magnetizable particles on the worked surface can be collected by means of the medical tool being guided a second time across the worked surface.

A medical tool as described here also comprises in particular a reservoir for receiving particles that have been attracted and collected by the magnet.

The reservoir is in particular designed in the form of a recess or depression or of a cavity open toward a surface of the medical tool. In particular, at least one pole surface of the magnet forms at least part of an inner surface of the reservoir. The pole surface or the pole surfaces of the magnet are in particular arranged in the reservoir in such a way that they are spaced apart from a plane defined by the edge of a recess forming the reservoir or are set back from this plane. In this case, the pole surface or the pole surfaces of the magnet cannot touch tissue across which the medical tool is guided, or they touch it only in the case of sufficient elasticity of the tissue. Particles attracted and collected by the magnet cannot therefore be stripped off, or easily stripped off, by a tissue surface, and instead they remain in the reservoir.

In a medical tool with a reservoir as described here, the reservoir has in particular an opening on a side of the medical tool directed away from an area of action of the removing device of the medical tool.

The area of action of the removing device is in particular the direct vicinity of a stationary blade and/or the area in which a rotatable or otherwise movable blade is movable. The arrangement of the opening of the reservoir, on the one hand, and of the area of action, on the other hand, on mutually opposite sides of the medical tool permits a selective use of the medical tool either for removing tissue or for attracting and collecting magnetic or magnetizable particles. By rotation of the medical tool about its longitudinal axis, it is possible to choose whether tissue is to be removed or whether magnetic or magnetizable particles are to be attracted and collected.

The opening of the reservoir and the area of action of the removing device can be arranged on mutually opposite sides of the medical tool. In this case, the medical tool has to be rotated substantially through 180 degrees in order to switch from one of the two functions (on the one hand tissue removal, and on the other hand attraction/collection of particles) to the other. Alternatively, the medical tool is designed such that a rotation through a smaller angle, for example 90 degrees, is needed for a switch between the two functions.

In a medical tool as described here, in particular at least one pole surface of the magnet is arranged on a side of the medical tool directed away from an area of action of the medical tool.

The arrangement of at least one pole surface of the magnet, on the one hand, and of the area of action, on the other hand, on sides of the medical tool directed away from each other permits a selective use of the medical tool either for removing tissue or for attracting and collecting magnetic or magnetizable particles. By rotation of the medical tool about its longitudinal axis, it is possible to choose whether tissue is to be removed or whether magnetic or magnetizable particles are to be attracted and collected.

The pole surface of the magnet and the area of action of the removing device can be arranged on mutually opposite sides of the medical tool. In this case, the medical tool has to be rotated substantially through 180 degrees in order to switch from one of the two functions (on the one hand tissue removal, and on the other hand attraction/collection of particles) to the other. Alternatively, the medical tool is designed such that a rotation through a smaller angle, for example 90 degrees, is needed for a switch between the two functions.

In a medical tool as described here, the removing device has in particular a magnetic or magnetizable material.

As has already been mentioned, a magnetic or magnetizable material means a material that is not just diamagnetic. In particular, a magnetic or magnetizable material is a paramagnetic, ferromagnetic, anti-ferromagnetic or ferrimagnetic material. The use of a magnetic or magnetizable material on the removing device has the effect that particles released from the removing device can be attracted and collected by the magnet on account of their magnetic or magnetizable property. Therefore, compared to what was previously the case, no particles or substantially fewer particles resulting from abrasion need to remain behind in an operating site.

In a medical tool as described here, the removing device has in particular a geometrically defined blade.

The removing device comprises in particular a milling cutter with one, two, three, four or more geometrically defined blades. Alternatively or in addition, the removing device can have a grinding device with geometrically undefined blades.

In a medical tool as described here, the removing device has in particular two blades which are designed and arranged to be moved past each other in order to remove tissue.

In particular, one or more blades are arranged on a stationary outer shank, and one or more blades are arranged on an inner shank. The inner shank is in particular arranged and designed in the outer shank in order to rotate about a common longitudinal axis of the outer shank and of the inner shank. Between the two or more blades moved past each other, the tissue is cut through by a shearing action.

A medical instrument comprises a medical tool as described here.

In a method for removing tissue, tissue is removed by means of a medical tool, and magnetic or magnetizable particles that are produced during the removal are attracted by means of a magnet on the medical tool.

The method is in particular carried out using a medical tool or a medical instrument as described here.

In a method as described here, the particles are attracted in particular during or after the removal.

In a method as described here, the particles are in particular collected in a reservoir.

A method as described here also comprises, between the step of removal and the step of attraction, a step involving rotation of the medical tool.

Between the removal and the attraction, it is not just a part of the medical tool that is rotated, for example a rotatable inner shank or a rotatable milling cutter. Instead, the entire medical tool is rotated. In particular, the rotation of the medical tool comprises a rotation of an outer shank of the medical tool.

During the rotation of the medical tool after the removal of tissue and before the attraction of particles, an area of action of the medical tool is in particular rotated away from a surface from which tissue has been removed. At the same time, the magnet is rotated toward the surface from which tissue has been removed.

BRIEF DESCRIPTION OF THE DRAWINGS

Embodiments are explained in more detail below with reference to the accompanying figures, in which.

DETAILED DESCRIPTION OF THE INVENTION

Figure 1:
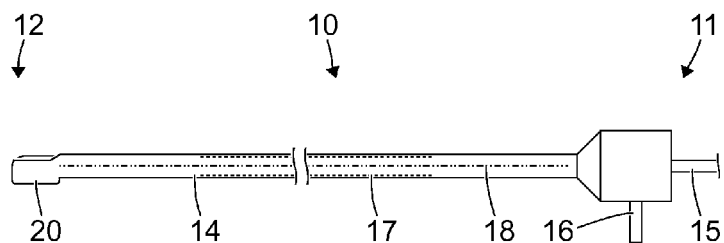
FIG. 1 shows a schematic view of a medical instrument.

FIG. 1 shows a schematic view of a medical instrument 10 with a proximal end 11, a distal end 12, and a shank 14 extending substantially from the proximal end 11 to the distal end 12. The shank 14 is in particular straight and rigid and has a cylindrical, in particular a circular cylindrical, lateral surface. Alternatively, the shank can be curved at least in parts and/or flexible at least in parts and/or can have a varying cross section.

A drive device 15 is provided at the proximal end 11 of the medical instrument 10. The drive device 15 is in particular a flexible shaft, or a coupling for coupling the medical instrument to a flexible shaft. By means of the flexible shaft, the proximal end 11 of the medical instrument 10 is connected or connectable to a motor, in particular an electric motor. Alternatively, the medical instrument 10 can itself have a motor at the proximal end 11, in particular an electric motor, a pneumatic motor or a hydraulic motor.

Moreover, the proximal end 11 of the medical instrument 10 has a suction nozzle 16 or a coupling for releasably connecting the medical instrument 10 to a pump or to a suction device or to a vacuum source for the suction of free-flowing material.

In the shank 14, the medical instrument 10 has a shaft 17, of which only a portion is indicated in FIG. 1 by broken lines. The shaft 17 is rotatable in the shank 14 and in particular about a common axis of symmetry 18 of the shank 14 and of the shaft 17. At the proximal end 11 of the medical instrument 10, the shaft 17 is coupled directly or indirectly to the drive device 15, such that the drive device 15 can rotate the shaft 17 about its axis of symmetry 18. If the shaft 17 is hollow or tubular, its lumen at the distal end 11 of the medical instrument 10 is coupled fluidically to the suction nozzle 16, such that fluids in the interior of the shaft 17 can be sucked from the distal end 12 to the proximal end 11 and to the suction nozzle 16.

At the distal end 12, the medical instrument 10 has a medical tool 20 for removing tissue. Illustrative embodiments of the tool 20 are set out below with reference to FIGS. 2 to 8.

Figure 2:
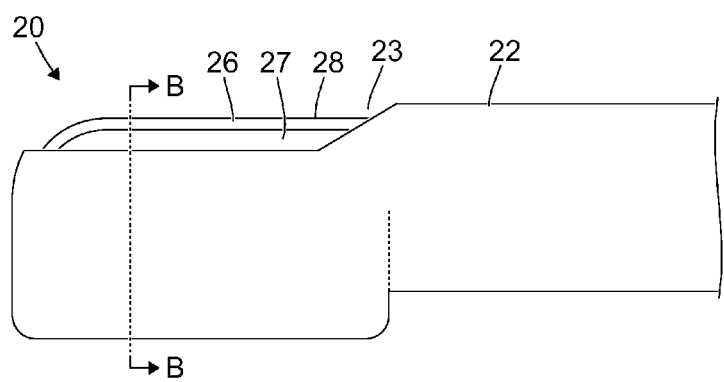
FIG. 2 shows a schematic view of a medical tool.

FIG. 2 shows a schematic view of an embodiment of the tool 20 at the distal end 12 of the medical instrument from FIG. 1. The medical tool 20 comprises an outer shank 22, which can be formed in one piece with the shank 14 of the medical instrument 10 (compare FIG. 1). In particular, the distal end of the shank 14 of the medical instrument 10 forms the outer shank 22 of the medical tool 20. Alternatively, the outer shank 22 of the medical tool 20 is mechanically coupled, for example via coupling mechanisms, to the shank 14 of the medical instrument 10 such that they are detachable without destruction.

The outer shank 22 has a window-shaped opening 23 through which a part of a rotatable inner shank 26 is visible. On account of the angle position of the inner shank 26 depicted in FIG. 2, a blade 28 is visible at the edge of an opening 27 on the inner shank 26. The blade 28 extends parallel or substantially parallel to the drawing plane of FIG. 2.

Figure 3:
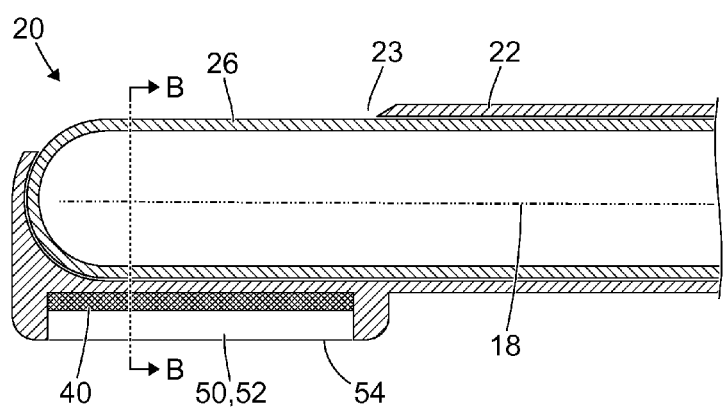
FIG. 3 shows a schematic cross-sectional view of the medical tool from FIG. 2.

FIG. 3 shows a schematic cross-sectional view of the medical tool 20 from FIG. 2. The sectional plane A-A depicted is parallel to the drawing planes of FIGS. 1 and 2 and contains the longitudinal axis 18 of the medical instrument 10 or of the shank 14 of the medical instrument 10 (cf. FIG. 1). The inner shank 26 has a substantially circular cylindrical shape and is rotatable in the outer shank 22, about the longitudinal axis 18, with little play and little friction.

A magnet 40 is arranged in a reservoir 50 or in an interior 52 of the reservoir 50. The reservoir 50 has an opening 54 on a side directed away from the opening 23 on the outer shank 22. To put it another way, the opening 23 in the outer shank 22 and the opening 54 of the reservoir 50 lie on mutually opposite sides of the medical tool 20, in particular of the outer shank 22.

Figure 4:
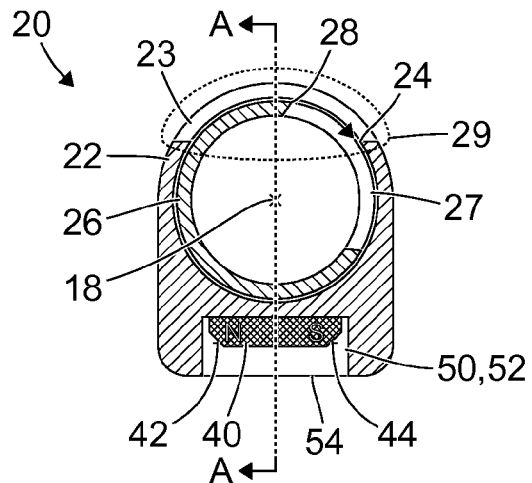
FIG. 4 shows another schematic cross-sectional view of the medical tool from FIGS. 2 and 3.

FIG. 4 shows another schematic cross-sectional view of the medical tool 20 from FIGS. 2 and 3. The sectional plane B-B of FIG. 4 is perpendicular to the drawing plane of FIG. 2, perpendicular to the sectional plane A-A of FIG. 3 and perpendicular to the longitudinal axis 18. The position of the sectional plane B-B of FIG. 4 is indicated in FIGS. 2 and 3. The position of the sectional plane A-A of FIG. 3 is indicated in FIG. 4.

Some of the features of the medical tool 20 that have already been described above with reference to FIGS. 2 and 3 can be seen in FIG. 4. In particular, a blade 24 can be seen at the edge of the opening 23 on the outer shank 22, and a blade 28 can be seen at the edge of the opening 27 on the inner shank 26. In the example shown, the respectively opposite edges of the opening 23 on the outer shank 22 and of the opening 27 on the rotatable inner shank 26 are likewise designed as blades. In FIG. 4, an arrow indicates a rotation movement of the inner shank 26 during which tissue sucked through the opening 23 on the outer shank 22 and the opening 27 on the inner shank 26 into the interior of the inner shank 26 is cut through by a shearing movement of the two blades 24, 28 relative to each other.

FIG. 4 also shows the arrangement of the reservoir 50 and of the opening 54 of the reservoir 50 on a side directed away from the opening 23 on the outer shank 22. The opening 23 on the outer shank 22 and the opening 54 on the reservoir 50 are thus oriented in opposite directions, as has already been mentioned above in connection with FIG. 3.

In the interior 52 of the reservoir 50, the magnet 40 is arranged symmetrically with respect to the sectional plane A-A of FIG. 3. The north pole and south pole of the magnet 40 and associated pole surfaces 42, 44 are accordingly arranged symmetrically with respect to the sectional plane A-A. The magnet 40 is substantially cuboid. The pole surfaces 42, 44 of the magnet 40 comprise chamfers or bevels, which are in part directed toward the opening 54 of the reservoir 50. The magnet 40 is in particular magnetized such that the magnetic field leaving or entering at the pole surfaces 42, 44 is concentrated to the highest possible extent in the interior 52 of the reservoir 50 and in the space adjoining the opening 54 of the reservoir 50, and to the lowest possible extent in the outer shank 22. For this purpose, the magnet 40 can have a shape differing from the views in FIGS. 3 and 4.

The magnet 40 only partially fills the recess in the outer shank forming the reservoir 50. The area of the recess not filled by the magnet 40 is designated as the interior 52 of the reservoir 50. The pole surfaces 42, 44 of the magnet 40 form a part of the inner surface of the reservoir 50.

The magnet 40 is set back with respect to the opening 54 of the reservoir 50. To put it another way, the magnet 40 is spaced apart from the opening 54 of the reservoir 50. In particular, the edge of the opening 54 of the reservoir 50 lies in a plane spaced apart from the magnet 40. For this reason, particles adhering to the pole surfaces 42, 44 of the magnet 40 do not touch, or do not easily touch, tissue across which the reservoir 50 with the magnet 40 is guided. This therefore reduces the risk that particles adhering to the pole surfaces 42, 44 are stripped off from the pole surfaces 42, 44 by tissue.

The medical tool shown in FIGS. 2 to 4 can be used alternately to remove tissue from a surface by means of the blades 24, 28. For this purpose, the surface to be worked, or the surface from which tissue is to be removed, is brought into the area of action of the blades 24, 28, which is indicated by a broken-line contour 29 in FIG. 4. In terms of the interaction with tissue, it is possible for the blades 24, 28, or the removing device formed by the blades 24, 28 (also in a departure from the view in FIGS. 2 to 4), to have properties and features similar to those of the aforementioned DE 10 2006 034 756 A1 and DE 10 2009 010 561 A1.

After a rotation of the medical tool 20 through 180 degrees about the longitudinal axis 18, the opening 54 of the reservoir 50 can be guided across the previously worked surface. The magnet 40 attracts magnetic or magnetizable particles which, for example, have been generated by wear on the outer shank 22 and on the inner shank 26, and collects these particles in the reservoir 50.

Figure 5:
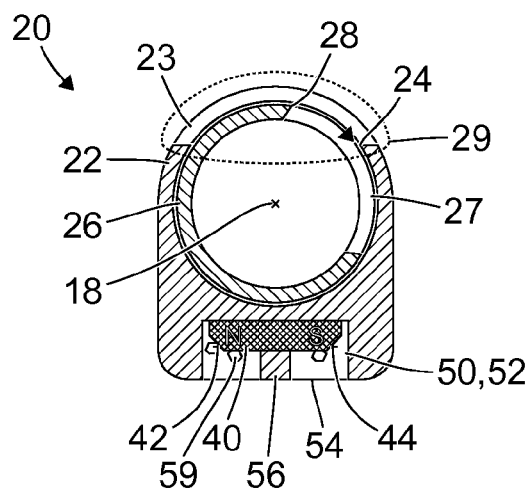
FIG. 5 shows a schematic cross-sectional view of another medical tool.

FIG. 5 shows a schematic cross-sectional view of another medical tool 20 which, in some features and properties, is similar to the medical tool set out above with reference to FIGS. 2 to 4. Below, only those features and properties are described in which the medical tool 20 according to FIG. 5 differs from the medical tool set out above with reference to FIGS. 2 to 4. The sectional plane of FIG. 5 corresponds to the sectional plane of FIG. 4.

In the interior 52 of the reservoir 50, a web 56 is arranged which reaches from the magnet 40 to as far as the plane defined by the edge of the opening 54 of the reservoir 50. The web 56 is in particular made of a non-magnetic and non-magnetizable material. The web 56 divides the reservoir 50 into two substantially symmetrical subregions and reduces the risk of elastic tissue penetrating far into the interior 52 of the reservoir 50 and there touching the pole surfaces 42, 44 of the magnet 40. The web 56 thus reduces the risk that particles 59 adhering to the pole surfaces 42, 44 are stripped off again from the pole surfaces 42, 44 by tissue.

Moreover, the web 56 reduces the probability of magnetic or magnetizable particles forming a bridge between the pole surfaces 42, 44 of the magnet 40 and magnetically short-circuiting these. The web 56 thus helps ensure that the force of attraction exerted on magnetic or magnetizable particles 59 by the magnet is maintained for longer.

Figure 6:
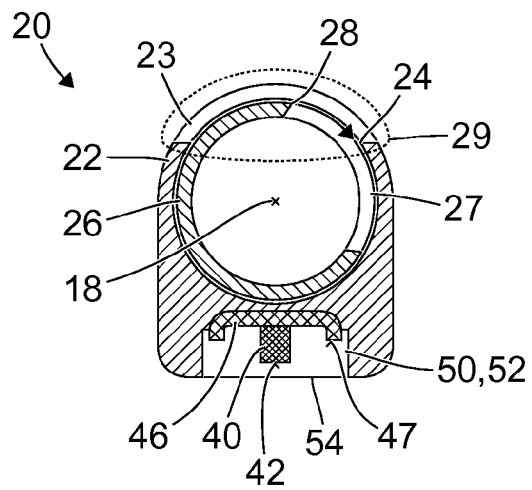
FIG. 6 shows a schematic cross-sectional view of another medical tool.

FIG. 6 shows a schematic cross-sectional view of another medical tool 20 which, in some features and properties, is similar to the medical tools set out above with reference to FIGS. 2 to 5. Below, only those features and properties are described in which the medical tool according to FIG. 6 differs from the medical tools set out above with reference to FIGS. 2 to 5. The sectional plane of FIG. 6 corresponds to the sectional planes of FIGS. 4 and 5.

In the reservoir 50, a pole of the magnet 40 is adjoined by a magnetic flux conductor 46 made of a magnetizable material. The magnet 40 and the magnetic flux conductor 46 are arranged in a symmetrical configuration, which is T-shaped in the cross section shown. In addition to the pole surface 42 on the magnet 40, forming for example the north pole of the magnet 40 itself, two further pole surfaces 47 (south poles in the stated example) therefore form parts of the inner surface of the interior 52 of the reservoir 50. The number of pole surfaces 42, 47 in the medical tool 20 from FIG. 6 is greater compared to the medical tools from FIGS. 2 to 5, and this can simplify the collection of magnetic or magnetizable particles.

Figure 7:
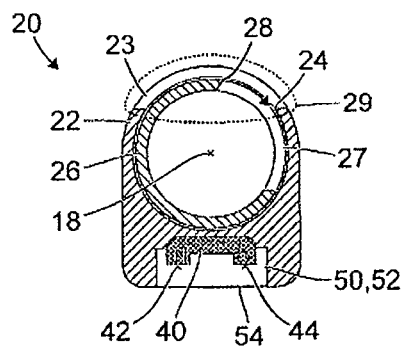
FIG. 7 shows a schematic cross-sectional view of another medical tool.

FIG. 7 shows a schematic cross-sectional view of another medical tool 20 which, in some features and properties, is similar to the medical tools set out above with reference to FIGS. 2 to 6. Below, only those features and properties are described in which the medical tool according to FIG. 7 differs from the medical tools set out above with reference to FIGS. 2 to 6. The sectional plane of FIG. 7 corresponds to the sectional planes of FIGS. 4 to 6.

In the medical tool 20 from FIG. 7, the magnet 40 has a substantially U-shaped cross section. The pole surfaces 42, 44 of the magnet 40 are substantially parallel to each other and parallel to the plane defined by the edge of the opening 54 of the reservoir 50. This design of the magnet 40 can help ensure that the magnetic field generated by the magnet 40 is concentrated substantially within the interior 52 of the reservoir 50 and into the area adjacent via the opening 54. In this way, the collecting properties of the magnet 40 can be improved.

Figure 8:
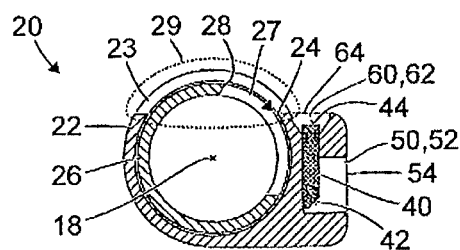
FIG. 8 shows a schematic cross-sectional view of another medical tool.

FIG. 8 shows a schematic cross-sectional view of another medical tool 20 which, in some features and properties, is similar to the medical tools set out above with reference to FIGS. 2 to 7. Below, only those features and properties are described in which the medical tool according to FIG. 8 differs from the medical tools set out above with reference to FIGS. 2 to 7. The sectional plane of FIG. 8 corresponds to the sectional planes of FIGS. 4 to 7.

The medical tool 20 from FIG. 8 has two reservoirs 50, 60 which are spatially separate and spaced apart from each other. The magnet 40 is arranged such that a pole of the magnet 40 lies on the first reservoir 50, and the other pole of the magnet 40 lies on the second reservoir 60. A first pole surface 42 of the magnet 40 forms part of the inner surface of the interior 52 of the first reservoir 50. A second pole surface 44 of the magnet 40 forms part of the inner surface of the interior 62 of the second reservoir 60. Both pole surfaces 42, 44 are set back, in the sense described above, from the openings 54, 64 of the associated reservoirs 50, 60.

The reservoirs 50, 60 and their openings 54, 64 are oriented in different directions. The opening 54 of the first reservoir 50 is oriented such that, after removal of tissue by means of the removing device formed by the blades 24, 28, the medical tool 20 has to be rotated through an angle of 90 degrees about the longitudinal axis 18 in order to ensure that, by means of the first pole surface 42 of the magnet 40, magnetic or magnetizable particles on the worked surface are collected in the first reservoir 50. The second reservoir 60 and the opening 62 of the second reservoir 60 are arranged and oriented in such a way that, even when tissue is being removed from a surface by means of the removing device formed by the blades 24, 28, magnetic or magnetizable particles from the surface can be collected in the second reservoir 60. To put it another way, the second reservoir 60 and the opening 64 of the second reservoir 60 lie alongside the removing device 24, 28 and alongside the area of action 29 thereof.

In a departure from the view in FIG. 8, one or more dedicated magnets can be provided for each reservoir 50, 60. In this case, all the pole surfaces of a first magnet form inner surfaces of the interior 52 of the first reservoir 50, and all the pole surfaces of a second magnet form inner surfaces of the interior 62 of the second reservoir 60. Moreover, a third reservoir can be provided symmetrically with respect to the second reservoir 60, such that there is a reservoir arranged to each side of the removing device 24, 28. With reservoirs arranged next to both sides of the removing device 24, 28, magnetic or magnetizable particles that are produced during removal of tissue can be collected irrespectively of the direction in which the tool 20 is moved (to the left or to the right in FIG. 8).

Some of the features of the medical tools set out with reference to FIGS. 2 to 8 can be combined in other ways than have been set out with reference to FIGS. 2 to 8. Moreover, the dimensions and cross sections of the magnet 40, of the reservoirs 50, 60, of the outer shank 22, of the rotatable inner shank 26 and of the blades 24, 28 can differ from the views in FIGS. 2 to 8. Instead of one magnet, it is possible to provide two or more magnets on one or more reservoirs 50, 60. Instead of having one opening 27, the rotatable inner shank 26 can have a plurality of openings with a corresponding plurality of blades 28.

Figure 9:
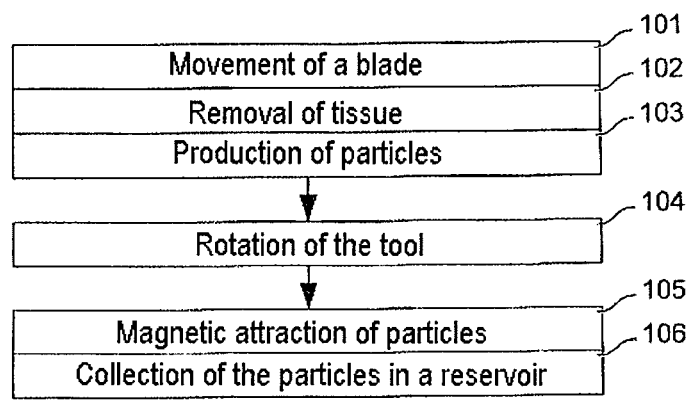
FIG. 9 shows a schematic flow chart of a method for removing tissue.

FIG. 9 shows a schematic flow chart of a method for removing tissue. The method can be carried out by means of a medical tool or medical instrument that has features and properties differing from those described with reference to FIGS. 1 to 8. For a better understanding, however, reference signs from FIGS. 1 to 8 are used below by way of example.

In a first step 101, a blade 28 is moved, in particular rotated. In a second step 102, tissue is removed by means of the moved blade 28. A stationary blade 24 may also be involved in the second step 102, in which case tissue is cut through in particular by a shearing motion of the blades 24, 28. In a third step 103, magnetic or magnetizable particles 59 are produced, in particular by attrition or wear of the blade 28 or of another part of a medical tool 20 that includes the blade 28. The first step 101, the second step 102 and the third step 103 are in particular carried out simultaneously, such that the rotation of the blade 28 causes tissue to be removed, in the process of which abraded material is produced in the form of particles.

In an optional fourth step 104, the tool 20 is rotated, in particular about its longitudinal axis and in particular through an angle of 180 degrees.

In a fifth step 105, magnetic or magnetizable particles 59 produced in the third step 103 are attracted by means of a magnet 40. In a sixth step 106, the particles 59 attracted in the fifth step 105 are collected in a reservoir 50, 60. The fifth step 105 and the sixth step 106 are carried out using the same medical tool 20 with which the first step 101, the second step 102 and the third step 103 are carried out. The fifth step 105 and the sixth step 106 are in particular carried out simultaneously or substantially simultaneously, the magnetic or magnetizable particles 59 being drawn into the reservoir 50, 60 by the magnet 40.

The first step 101, the second step 102 and the third step 103 on the one hand, and the fifth step 105 and the sixth step 106 on the other hand, can be carried out simultaneously or in direct succession in a continuous application of the medical tool 20. In this case, the fourth step 104 is omitted. Alternatively, the fifth step 105 and the sixth step 106 are carried out separately after the medical tool 20, in the fourth step 104, has been rotated with respect to the orientation in the first step 101, in the second step 102 and in the third step 103 by a predetermined angle (for example 180 degrees in the case of the examples set out above with reference to FIG. 2 to 8, or 90 degrees in the case of the example set out above with reference to FIG. 8).

REFERENCE SIGNS 10 medical instrument
11 proximal end of the medical instrument 10
12 distal end of the medical instrument 10
14 shank of the medical instrument 10
15 drive device at the proximal end 11 of the medical instrument 10
16 suction nozzle
17 shaft between drive device 15 and tool 20
18 axis of symmetry of the shank 14
20 medical tool
22 outer shank of the tool 20
23 opening on the outer shank of the tool 20
24 blade on the outer shank 22
26 rotatable inner shank of the tool 20
27 opening on the inner shank 20
28 blade on the rotatable inner shank 26
29 area of action of the blades 24, 28
40 magnet
42 first pole surface of the magnet 40
44 second pole surface of the magnet 40
46 magnetic flux conductor
47 pole surface on the magnetic flux conductor
50 reservoir on the medical tool 20
52 interior of the reservoir 50
54 opening of the reservoir 50
56 web
59 magnetic or magnetizable particle
60 further reservoir on the medical tool 20
62 interior of the reservoir 60
64 opening of the reservoir 60
101 first step (movement, in particular rotation, of a blade)
102 second step (removal of tissue)
103 third step (production of magnetic or magnetizable particles)
104 fourth step (rotation of the tool)
105 fifth step (attraction of the particles by magnets)
106 sixth step (collection of the particles in a reservoir)

The invention claimed is:

1. A medical tool for removing tissue comprising:
a removing device for mechanical removal of tissue the removing device having magnetic or magnetizable materials on the surfaces of the removing device that are affected by abrasion or erosion, such that magnetic or magnetizable particles are produced from the magnetic or a magnetizable materials during the mechanical removal of tissue;
a magnet for magnetic attraction and collection of the magnetic or magnetizable particles.

2. The medical tool according to claim 1, wherein the magnet is arranged on a component of the tool that is substantially stationary during removal of tissue.

3. The medical tool according to claim 1, wherein the removing device comprises a first component and a second component, the second component is movable relative to the first component in order to remove tissue,
the magnet is arranged on the first component,
a blade is arranged on the second component.

4. The medical tool according to claim 1, wherein the magnet is arranged and designed to collect particles during removal of tissue.

5. The medical tool according to claim 1, wherein the medical tool is configured to be rotatable about its longitudinal axis after removal of tissue, and
wherein the magnet is configured to collect the magnetic or magnetizable particles after the rotation of the medical tool about its longitudinal axis.

6. The medical tool according to claim 1, further comprising a reservoir for receiving particles that have been attracted and collected by the magnet.

7. A medical tool for removing tissue comprising:
a removing device for the mechanical removal of tissue,
a magnet for the magnetic attraction and collection of magnetic or magnetizable particles, and
a reservoir for receiving particles that have been attracted and collected by the magnet;
wherein the reservoir has an opening on a side of the medical tool directed away from an area of action of the removing device of the medical tool.

8. The medical tool according to claim 1, wherein at least one pole surface of the magnet is arranged on a side of the medical tool directed away from an area of action of the medical tool.

9. The medical tool according to claim 1, wherein the removing device has two blades which are designed and arranged to be moved past each other in order to remove tissue.

10. A medical instrument for removing tissue comprising:
a first shank extending substantially from a proximal end to a distal end,
a medical tool according to claim 1 for removing tissue, the medical tool comprising an outer shank, the outer shank coupled with the first shank at the distal end,
a shaft inside the first shank, the shaft rotatable about a common axis of symmetry of the first shank and of the shaft,
a drive device positioned at the proximal end of the first shank and coupled directly or indirectly to the shaft for rotating the shaft,
a suction nozzle positioned at the proximal end of the first shank for suction of free-flowing material.

11. A method for removing tissue, comprising:
tissue is removed by means of a medical tool, the medical tool having magnetic or magnetizable materials on the surface areas of the medical tool that are affected by abrasion or erosion;
magnetic or magnetizable particles are produced from the magnetic or magnetizable materials by abrasion during the removal of tissue;
the magnetic or magnetizable particles are attracted by means of a magnet on the medical tool.

12. The method according to claim 11, wherein the particles are attracted during or after the removal of tissue.

13. The method according to claim 11, further comprising the following step:
   the magnetic or magnetizable particles are collected in a reservoir.

14. The method according to claim 11, further comprising the following step between the step of removal of tissue and the step of attraction of magnetic or magnetizable particles:
   rotation of the medical tool.

15. The medical tool of claim 3, wherein the magnetic or magnetizable materials are used on the surface of the blade.

* * * * *